(12) United States Patent
Kamire et al.

(10) Patent No.: US 11,519,079 B2
(45) Date of Patent: Dec. 6, 2022

(54) ELECTROCHEMICAL CARBON DIOXIDE CONVERTER AND LIQUID REGENERATOR

(71) Applicant: HONEYWELL INTERNATIONAL INC., Charlotte, NC (US)

(72) Inventors: Rebecca Kamire, Vernon Hill, IL (US); Stephen Yates, South Barrington, IL (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 120 days.

(21) Appl. No.: 17/177,760

(22) Filed: Feb. 17, 2021

(65) Prior Publication Data

US 2021/0172075 A1 Jun. 10, 2021

Related U.S. Application Data

(60) Division of application No. 15/985,475, filed on May 21, 2018, now Pat. No. 10,941,497, which is a
(Continued)

(51) Int. Cl.
*B01D 53/22* (2006.01)
*C25B 1/04* (2021.01)
(Continued)

(52) U.S. Cl.
CPC ............. *C25B 1/04* (2013.01); *B01D 53/1425* (2013.01); *B01D 53/1475* (2013.01); *B01D 53/326* (2013.01); *B01D 53/75* (2013.01); *B01D 2252/30* (2013.01); *B01D 2256/10* (2013.01); *B01D 2256/12* (2013.01);
(Continued)

(58) Field of Classification Search
CPC ....... Y02P 20/151; Y02C 20/40; Y02E 60/36; B01D 53/326; B01D 2257/108; B01D 2257/502; B01D 2256/16; B01D 2252/30; B01D 2256/20; B01D 2257/504; B01D 53/1475; B01D 2256/12; B01D 2256/10;
(Continued)

(56) References Cited

U.S. PATENT DOCUMENTS 2,021,690 A   11/1935   Kaufman
2,035,478 A    3/1936   Houdry
(Continued)

FOREIGN PATENT DOCUMENTS

PL         217130 B1    6/2014
WO      2016178590 A1   11/2016

OTHER PUBLICATIONS

Muscatello et. al, 'Mars Atmospheric in Situ Resource Utilization Projects at the Kennedy Space Center', Earth & Space Conf. 2016, https://ntrs.nasa.gov/search.jsp?R=2016005187.
(Continued)

*Primary Examiner* — Anthony R Shumate
(74) *Attorney, Agent, or Firm* — Lorenz & Kopf, LLP

(57) ABSTRACT

A carbon dioxide conversion system for an environment includes a first gas-liquid contactor-separator downstream of the environment; an electrochemical conversion cell downstream of the first gas-liquid contactor-separator; and a cleaned ionic liquid storage intermediate the first gas-liquid contactor-separator and the electrochemical conversion cell.

7 Claims, 9 Drawing Sheets

Related U.S. Application Data continuation-in-part of application No. 15/896,150, filed on Feb. 14, 2018, now Pat. No. 11,123,685, and a continuation-in-part of application No. 15/896,156, filed on Feb. 14, 2018, now Pat. No. 10,688,435.

(60) Provisional application No. 62/463,921, filed on Feb. 27, 2017.

(51) Int. Cl.

| | | |
|---|---|---|
| *B01D 53/32* | (2006.01) | |
| *B01D 53/75* | (2006.01) | |
| *B01D 53/14* | (2006.01) | |
| *C07C 9/04* | (2006.01) | |
| *C07C 1/04* | (2006.01) | |

(52) U.S. Cl.
CPC ...... *B01D 2256/16* (2013.01); *B01D 2256/20* (2013.01); *B01D 2257/108* (2013.01); *B01D 2257/502* (2013.01); *B01D 2257/504* (2013.01); *B01D 2259/4575* (2013.01); *C07C 1/04* (2013.01); *C07C 9/04* (2013.01); *Y02C 20/40* (2020.08); *Y02E 60/36* (2013.01); *Y02P 20/151* (2015.11)

(58) Field of Classification Search
CPC ........ B01D 53/1425; B01D 2259/4575; B01D 53/75; C25B 1/04; C07C 9/04; C07C 1/04
See application file for complete search history.

(56) References Cited

U.S. PATENT DOCUMENTS

| | | | |
|---|---|---|---|
| 2,412,110 A | 12/1946 | Williams | |
| 2,450,707 A | 10/1948 | Zwickl | |
| 2,466,779 A | 4/1949 | Pevney | |
| 3,102,399 A | 9/1963 | Meckler | |
| 3,277,954 A | 10/1966 | Meckler | |
| 3,435,592 A | 4/1969 | Lindenmaier | |
| 3,852,180 A | 12/1974 | Gregory | |
| 4,109,877 A * | 8/1978 | Yates | B65H 67/04 242/486.7 |
| 4,112,662 A * | 9/1978 | Lappage | B65H 54/02 242/472.2 |
| 4,208,199 A | 6/1980 | Nakazato et al. | |
| 4,248,037 A * | 2/1981 | Martin | D01H 4/48 57/263 |
| 4,347,705 A | 9/1982 | Mirante | |
| 4,414,191 A | 11/1983 | Fuderer | |
| 4,861,351 A | 8/1989 | Nicholas et al. | |
| 4,997,630 A | 3/1991 | Wagner et al. | |
| 5,096,470 A | 3/1992 | Krishnamurthy | |
| 5,997,594 A | 12/1999 | Edlund et al. | |
| 6,428,608 B1 * | 8/2002 | Shah | B01D 53/261 95/126 |
| 7,687,048 B1 | 3/2010 | Schultz et al. | |
| 8,658,016 B2 | 2/2014 | Lakkaraju et al. | |
| 8,722,003 B1 | 5/2014 | Avagliano et al. | |
| 9,782,719 B1 * | 10/2017 | Iyer | B01D 53/1493 |
| 10,688,435 B2 | 6/2020 | Henson et al. | |
| 10,941,497 B2 | 3/2021 | Kamire et al. | |
| 2002/0083829 A1 | 7/2002 | Edlund et al. | |
| 2003/0056652 A1 | 3/2003 | Edlund et al. | |
| 2003/0069295 A1 * | 4/2003 | Yates | A61K 31/4164 514/396 |
| 2004/0265199 A1 | 12/2004 | MacKnight | |
| 2005/0132883 A1 | 6/2005 | Su et al. | |
| 2007/0051238 A1 | 3/2007 | Jain et al. | |
| 2008/0107571 A1 * | 5/2008 | Johnson | C01B 32/50 422/139 |
| 2008/0128048 A1 * | 6/2008 | Johnson | B64D 37/32 141/59 |
| 2010/0011956 A1 * | 1/2010 | Neumann | B01D 53/62 261/23.1 |
| 2010/0193370 A1 | 8/2010 | Olah et al. | |
| 2012/0014851 A1 | 1/2012 | Kloosterman et al. | |
| 2012/0247327 A1 | 10/2012 | Omole | |
| 2014/0065054 A1 | 3/2014 | Noyes | |
| 2014/0283839 A1 | 9/2014 | Wickham et al. | |
| 2014/0322118 A1 | 10/2014 | Vera-Castaneda | |
| 2014/0336428 A1 | 11/2014 | Banerjee et al. | |
| 2016/0016111 A1 | 1/2016 | Sirkar | |
| 2016/0039724 A1 * | 2/2016 | Naterer | C25B 1/26 422/162 |
| 2016/0289143 A1 * | 10/2016 | Duggal | C07C 7/152 |
| 2017/0107162 A1 * | 4/2017 | Duggal | B01D 53/228 |
| 2018/0169561 A1 | 6/2018 | Jonnavittula et al. | |
| 2018/0265993 A1 | 9/2018 | Kamire et al. | |
| 2020/0061523 A1 | 2/2020 | Cullinane | |
| 2022/0136119 A1 * | 5/2022 | Flanders | C12P 5/023 435/71.1 |

OTHER PUBLICATIONS

Holquist et. al, 'Electrochemical Carbon Dioxide Reduction with Room Temperature Ionic Liquids for Space Exploration Missions', 46th International Conference on Environmental Systems Jul. 10-14, 2016, Vienna, Austria, ICES-2016-314.

Lueck et. al, 'A Survey of Alternative Oxygen Production Technologies', http://ntrs.nasa.gov/search.jsp?R=20020000946.

Alvarez-Guerra et. al, 'Ionic liquids in the electrochemical valorisation of CO2', Energy Environ. Sci., 2015, 8 2574, Published on Jun. 16, 2015, pp. 2574-2599.

Asadi et. al, 'Robust carbon dioxide reduction on molybdenum disulphide edges', Nature Coomunications, 5:4470 DOI:10.1038/ncomms5470, Published Jul. 30, 2014.

Muscatello et. al, 'Evaluation of Mars CO2 Capture and Gas Separation Technologies', http://ntrs.nasa.gov/search.jsp?R=20110015862.

John Wiley & Sons, Inc, Electrochemical Processing, Organic, vol. 9, Kirk-Othmer Encyclopedia of Chemical Technology, pp. 652-685.

Gibson et. al, Novel Electrochemical Cell Designs for Simultaneous Production of Methane and Oxygen via the Electrolysis of Carbon Dioxide and Water, John F. Kennedy Space Center, NASA Tech Briefs, Feb. 2017.

Koh et. al, Oxygen Plasma Induced Hierarchically Structured Gold Electrocatalyst for Selective Reduction of Carbon Dioxide to Carbon Monoxide, The Journal of Physical Chemistry, C 2015, 119, 883-889, Published Dec. 17, 2014.

Muscatello et. al, 'Mars In Situ Resource Utilization Technology Evaluation', 50th AIAA Aerospace Sciences Meeting including the New Horizons Forum and Aerospace Exposition Jan. 9-12, 2012, Nashville, Tnnesee, AIAA 2012-0360.

Rosen et. al, 'Ionic Liquid-Mediated Selective Conversion of CO2 to CO at Low Overpotentials', Science vol. 334, Nov. 4, 2011, 643-645.

* cited by examiner

ELECTROCHEMICAL CARBON DIOXIDE CONVERTER AND LIQUID REGENERATOR

CROSS-REFERENCE TO RELATED APPLICATIONS

This application is a divisional application of U.S. patent application Ser. No. 15/985,475, filed May 21, 2018, which claims the benefit of and priority to U.S. patent application Ser. No. 15/896,150, filed Feb. 14, 2018, and which claims the benefit of U.S. provisional application Ser. No. 62/463,921, filed Feb. 27, 2017; and U.S. patent application Ser. No. 15/896,156, filed Feb. 14, 2018 and which claims the benefit of U.S. provisional application Ser. No. 62/463,921, filed Feb. 27, 2017; all of which are incorporated herein by reference.

BACKGROUND OF THE INVENTION

The present invention generally relates to carbon dioxide conversion and, more particularly, to apparatus and methods of carbon dioxide conversion employing gas-liquid contact and separation and electrochemical cells.

Long duration human space travel, such as to Mars, will require a life support system capable of recovering oxygen (O2) in high yield from carbon dioxide (CO2) exhaled by astronauts. The technological challenge falls only after spacecraft weight and susceptibility to radiation as a hurdle to long term habitation in space. On the International Space Station, CO2 is removed from the cabin by adsorption to solid sorbents. These are heavy and cannot be replaced or serviced in space. Accidental water exposure results in adsorbed water that is difficult to remove. In addition, a high regeneration temperature is required for CO2 desorption from the solid sorbents for downstream reaction with hydrogen (H2) in a Sabatier reactor to produce water. O2 is recovered from water via electrolysis. This is a very complicated system with many opportunities for failure and a maximum O2 yield of 50%.

Establishing an environment for human use on the planet Mars will require a source for oxygen for respiration and for propulsion. In addition to recovering oxygen from exhaled carbon dioxide, it may be useful to convert carbon dioxide from the Martian atmosphere into oxygen. The Martian atmosphere has an average pressure of 600 Pa (0.087 psi), and an average temperature of −55 degrees C. It has a composition comprising 96% CO2, 1.9% argon, and 1.9% nitrogen.

As can be seen, there is a need for improved apparatus and methods to remove carbon dioxide from a supply gas and convert it into oxygen in environments such as deep space vehicles.

SUMMARY OF THE INVENTION

In one aspect of the present invention, a carbon dioxide conversion system for an environment comprises a first gas-liquid contactor-separator downstream of the environment; an electrochemical conversion cell downstream of the first gas-liquid contactor-separator; and an ionic liquid storage intermediate the first gas-liquid contactor-separator and the electrochemical conversion cell.

In a further aspect of the present invention, a carbon dioxide conversion system for an environment closed to ambient air or gas comprises a scrubber downstream of the environment; an electrochemical conversion cell downstream of the scrubber; and an ionic liquid storage intermediate the scrubber and the electrochemical conversion cell; wherein the scrubber is configured to receive contaminated air from the environment, receive cleaned liquid absorbent from the ionic liquid storage, and discharge cleaned air to the environment; and wherein the cell stack is configured to discharge oxygen to the environment.

In another aspect of the present invention, a carbon dioxide conversion system for an environment open to ambient air or gas comprises a scrubber downstream of the environment; an electrochemical conversion cell downstream of the scrubber; and an ionic liquid storage intermediate the scrubber and the electrochemical conversion cell; wherein the scrubber is configured to receive contaminated air from the environment, receive cleaned liquid absorbent from the ionic liquid storage, and discharge at least one of Ar, N2, and CO to the environment; and wherein the cell stack is configured to discharge at least one of O2, CO, and CH4 not to be returned to the environment.

These and other features, aspects and advantages of the present invention will become better understood with reference to the following drawings, description and claims.

DETAILED DESCRIPTION OF THE INVENTION

Figure 1:
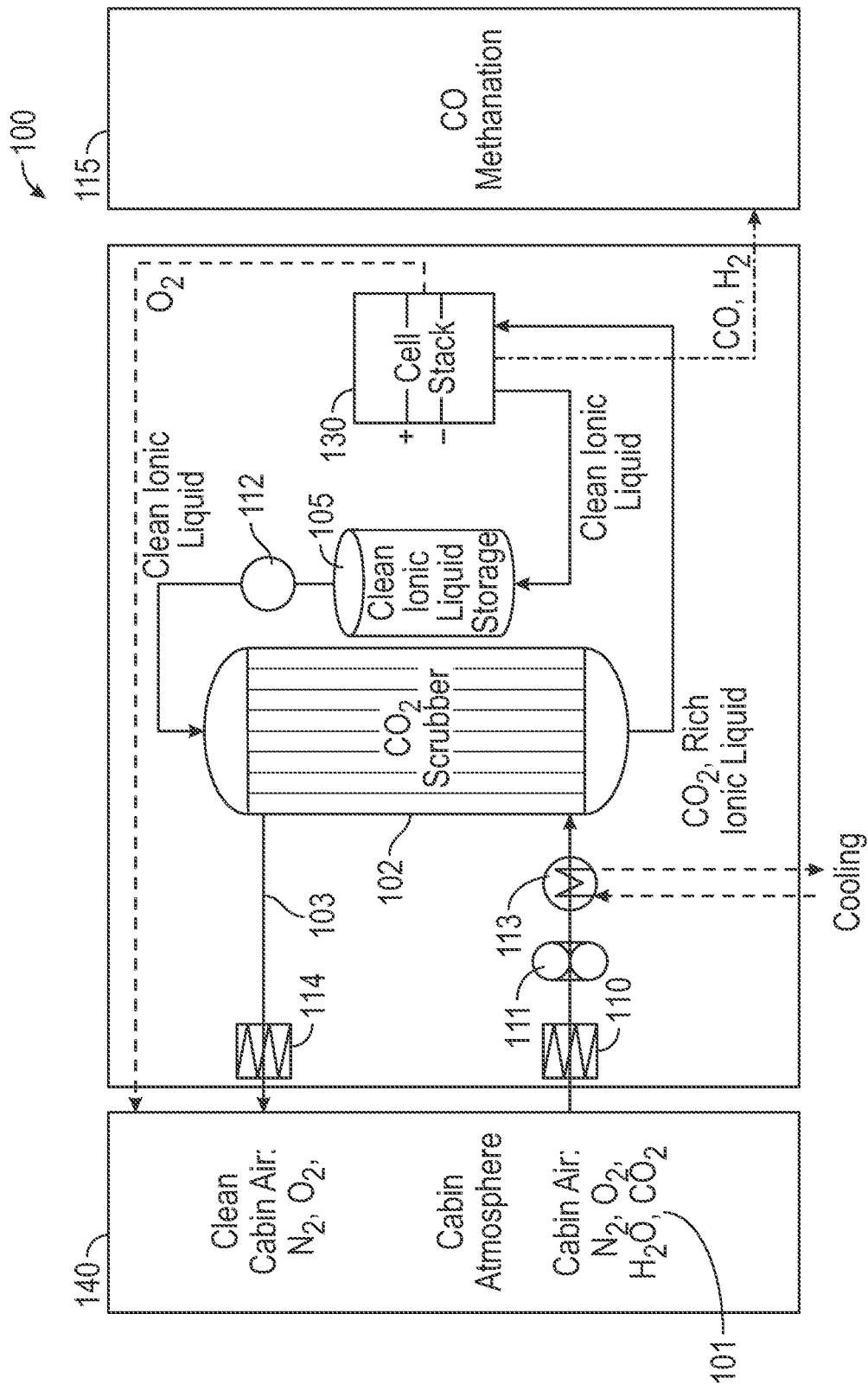
FIG. 1 is a schematic diagram of a carbon dioxide conversion system according to an embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

Broadly, the present invention can be integrated into environments such as spacecraft used in long-duration missions, specifically, space stations and spacecraft and habitats used in and beyond low earth orbit, as the invention, particularly gas-liquid separation, operates independent of gravity.

The present invention generally provides a Carbon Dioxide Removal by Ionic Liquid Sorbent (CDRILS) system wherein ionic liquids (ILs) can act as liquid $CO_2$ sorbents. In contrast to solid sorbents, liquid $CO_2$ sorbents can be more easily exchanged in space, while continuous flow processing has the potential to afford a more robust system and a lower overall mass. Select ILs have high capacities for $CO_2$, chemical and electrochemical stabilities, compatibilities with humidity in the gas stream, and negligible vapor pressures. The capacity of IL for both $CO_2$ and water allows for dual function $CO_2$ and humidity removal, while the chemical stability of both 1-butyl-3-methylimidazolium acetate (BMIM Ac) and 1-ethyl-3-methylimidazolium acetate (EMIM Ac) makes repeated absorption/desorption, temperature cycling, and electrochemical cycling possible. The lack of vapor pressure makes ILs particularly suited to the closed environments in space where any risk of air contamination or loss of liquids by evaporation outside the environment must be avoided. The CDRILS hollow fiber scrubber membranes provide high surface area for $CO_2$ sorption into the ILs. A subsequent stripper membrane removes the $CO_2$ at lower temperatures than those required for solid sorbents and regenerates the IL for recirculation to the scrubber.

The CDRILS system of the present invention can produce a $CO_2$-loaded IL and water mixture following the scrubber. The $CO_2$ Electrolysis in Ionic Liquid (CEIL) of the current invention can electrochemically convert the $CO_2$ and water directly to $O_2$ and reduced carbon species such as carbon monoxide (CO), methane ($CH_4$), and/or other products using IL as the electrolyte solution. The $O_2$ and reduced carbon products are easier to strip from the IL than $CO_2$.

When the CDRILS and CEIL systems are used for life support, production of $O_2$ and CO increases the maximum possible $O_2$ yield from $CO_2$ from 50% to 67%, when followed by a reactor configured for carbon monoxide methanation similar to a Sabatier reactor for carbon dioxide methanation. The reduced carbon species or further reduced products of the reactor may be transformed further to recover additional valuable products, or they can be used as fuels.

Additionally, the present invention could be used for In-situ Resource Utilization (ISRU) if the $CO_2$ source is the Mars atmosphere. If the desired target of ISRU is life support, $CO_2$ can be electrolyzed to CO and $O_2$. If the target is fuel generation for propulsion, $CO_2$ and water can be electrolyzed to CO, $H_2$, and/or methane ($CH_4$) and $O_2$. CO and $H_2$ would be further converted to $CH_4$ at a second catalyst, or electrochemically generated $CH_4$ could be utilized directly. The $O_2$ product would be stored for use when burning the fuel.

The present invention also enables water electrolysis to $H_2$ and $O_2$ in the same cell as $CO_2$ transformation. Water electrolysis in the same electrolysis cell(s) could eliminate the need for the current $O_2$ generation cell stack.

The invention uses a hollow fiber-based contactor for $CO_2$ and water removal from the cabin air or Mars atmosphere. The IL mixed with water is flowed through either the lumen or the shell of the hollow fiber module, while the cabin air or Mars atmosphere is flowed countercurrent through either the shell or the lumen respectively. The $CO_2$-loaded IL and water mixture is continuously flowed through the cathode compartment of an electrochemical conversion cell. The cathode compartment is separated from the anion compartment by an ion exchange membrane or porous separator. The anode compartment contains either a $CO_2$-free IL solution or an aqueous solution. A voltage is applied between the two electrodes to reduce $CO_2$ and water to reduced carbon species and $H_2$ and hydroxide at the cathode and oxidize water or hydroxide to $O_2$ at the anode. Additional cells can be stacked to provide the appropriate scaling for the necessary $O_2$ generation rate.

The $O_2$-laden liquid from the anode is then flowed to a stripper or centrifugal separator for $O_2$ separation, which can then be sent to the cabin or stored. The liquid is recycled to the anode compartment. The product-laden liquid from the cathode is flowed to a hollow fiber stripper. The liquid is flowed through the lumen or shell, while low pressure on the other side of the fiber strips the products and water from the IL to recover the mixture required for the scrubber inlet. The products are flowed to the methanation catalyst for water and methane production.

U.S. patent application entitled "Apparatus and Methods for Enhancing Gas-Liquid Contact/Separation" filed Feb. 1, 2017, Ser. No. 15/422,170; U.S. patent application entitled "Ionic Liquid $CO_2$ Scrubber for Spacecraft" filed Feb. 1, 2017, Ser. No. 15/422,166; U.S. patent application entitled "Hollow Fiber Membrane Contactor Scrubber/Stripper for Cabin Carbon Dioxide and Humidity Control" filed Feb. 14, 2018, Ser. No. 15/896,150; and U.S. patent application entitled "Dual Stripper with Water Sweep Gas" filed Feb. 14, 2018, Ser. No. 15/896,156, are incorporated herein by reference as though fully set forth herein.

Herein, the term "absorbent" is intended to generally include absorbents and/or adsorbents.

"Used liquid absorbent" means "clean liquid absorbent" that has absorbed carbon dioxide.

"Cleaned liquid absorbent" means liquid absorbent that is substantially free of absorbed carbon dioxide.

"Regenerated liquid absorbent" means used liquid absorbent that has undergone desorption of carbon dioxide.

"Cleaned gas" means gas that has an insubstantial amount of carbon dioxide and/or $H_2O$. "Cleaned gas" has a carbon dioxide and/or $H_2O$ concentration less than that of the gas from the environment to be cleaned.

FIG. 1 is a schematic diagram of an exemplary carbon dioxide conversion system (i.e., closed-loop air revitalization system) 100 that may be employed in a space-based system. A "closed-loop air revitalization system" is intended to mean a system which recovers valuable resources from waste products, such as recovering valuable oxygen from waste carbon dioxide. The system 100 may include one or more gas-liquid contactor-separators to effectuate removal of carbon dioxide However, the system 100 is not limited to the contactor-separators described below.

The carbon dioxide conversion system 100 may receive a contaminated air 101 from an enclosed environment 140 suitable for human occupants, such as a spacecraft cabin. Thus, the environment 140 can be configured to be closed to, or sealed from, ambient air or gas. The contaminated air or gas 101 may include one or more gas/vapor contaminants such as $N_2$, $CO_2$, and/or $H_2O$.

The air or gas 101 may flow into a first gas-liquid contactor-separator (i.e., scrubber) 102. In embodiments, the contaminated air 101 may, before entering the scrubber 102, be filtered for dust and particulates, via a filter 110, as well as being forced, via a fan or compressor 111, into the scrubber 102. In some embodiments, the contaminated air 101 may exit the fan 111 and enter a cooler 113 before entering the scrubber 102.

Concurrently with, or sequentially with, the scrubber 102 receiving the contaminated air 101, cleaned liquid absorbent may be pumped, via a pump 112, into the scrubber 102, from a cleaned liquid absorbent storage 105. In embodiments, the liquid absorbent may be one or more ionic liquids described below. In the scrubber 102, the cleaned ionic liquid(s) may absorb contaminants, such as CO2, from the contaminated air 101.

From the scrubber-separator 102, cleaned air 103 may optionally flow through a filter 114, to capture any leaked ionic liquid and/or produce a further cleaned air that can flow back to the environment 140 to be conditioned. In embodiments, the cleaned air 103 may have a gas contaminant(s) concentration, and/or H2O concentration, lower than that of the contaminated air 101.

Also from the scrubber-separator 102, used liquid absorbent may exit. The used liquid absorbent may flow into an electrochemical conversion cell 130 or, in embodiments, a plurality of electrochemical conversions cells. In embodiments, the plurality of cells may be in a stack configuration.

Figure 1A:
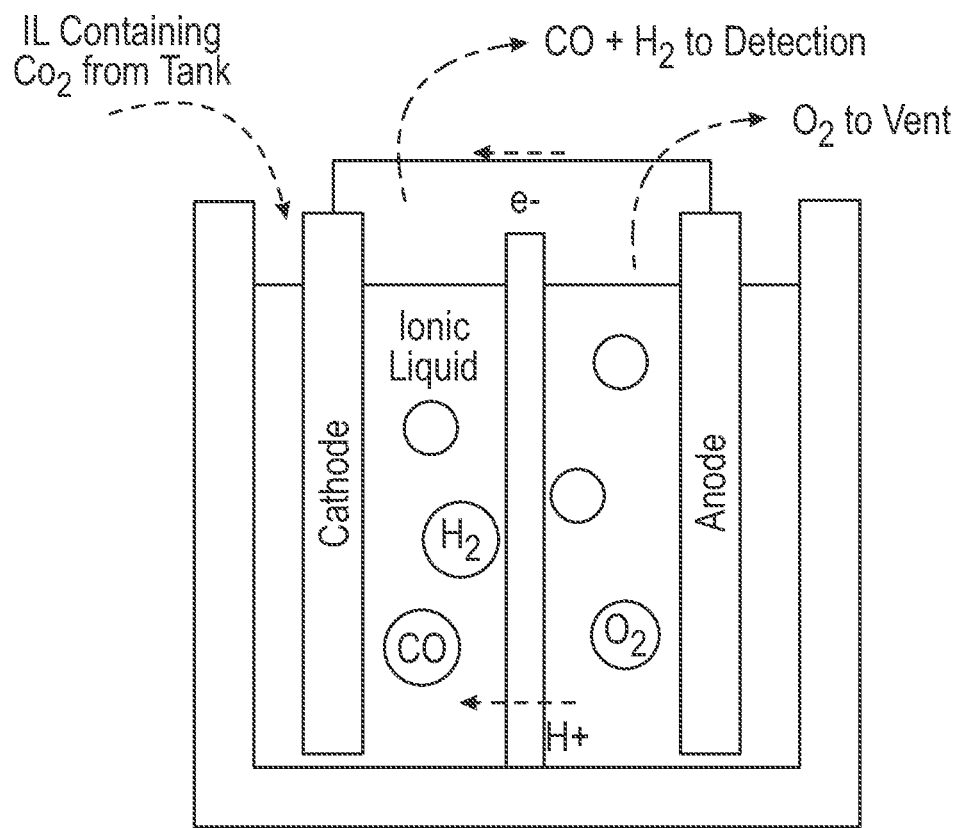
FIG. 1A is a schematic diagram of an electrochemical conversion cell in a carbon dioxide conversion system according to an embodiment of the present invention.

FIG. 1A schematically depicts an exemplary electrochemical conversion cell 130. The cell 130 may have an anode, cathode and an ionic membrane therebetween, all of which are in a bath of ionic liquid. The half reaction at the anode that generates oxygen is either 2 H2O→O2+4 H++4 e− or 4 OH−→2 H2O+4 e−+O2, depending on the pH. Multiple reactions are proposed to occur at the cathode. These include production of hydrogen: 2 H++2 e−→H2 or 2 H2O+2 e−→2 OH−+H2, and production of carbon monoxide: CO2+2H++2e−→CO+H2O or 2H2O+2 CO2+4 e−Δ2 CO+4 OH−. Under some circumstances, and depending on the cathode material, methane may also be generated: CO2+ 8H++8e−ΔCH4+2 H2O or 6 H2O+CO2+8 e−→CH4+8 OH−.

The cell 130 can receive a used ionic liquid having CO2. The cell 130 can discharge O2 to the environment 140. Concurrently with, or sequentially with, the O2 discharge, the cell 130 may discharge cleaned ionic liquid to the ionic liquid storage 105. Concurrently with, or sequentially with, the O2 and cleaned ionic liquid discharge, the cell 130 may discharge CO and/or H2 to a CO methanation reactor 115. The CO methanation reactor functions by reacting the carbon monoxide with hydrogen to convert it to methane and water. The water, in turn, may be electrolyzed to generate hydrogen and oxygen, forming a closed-loop air revitalization system.

As noted above, the electrochemical conversion cell 130 may be present in the form of a stack of cells. Such a stack may be as described in Fry, A. J., Electrochemical Processing, Organic. In *Kirk-Othmer Encyclopedia of Chemical Technology*, John Wiley & Sons, Inc.: 2000, FIG. 10, which is incorporated herein in its entirety.

Figure 2:
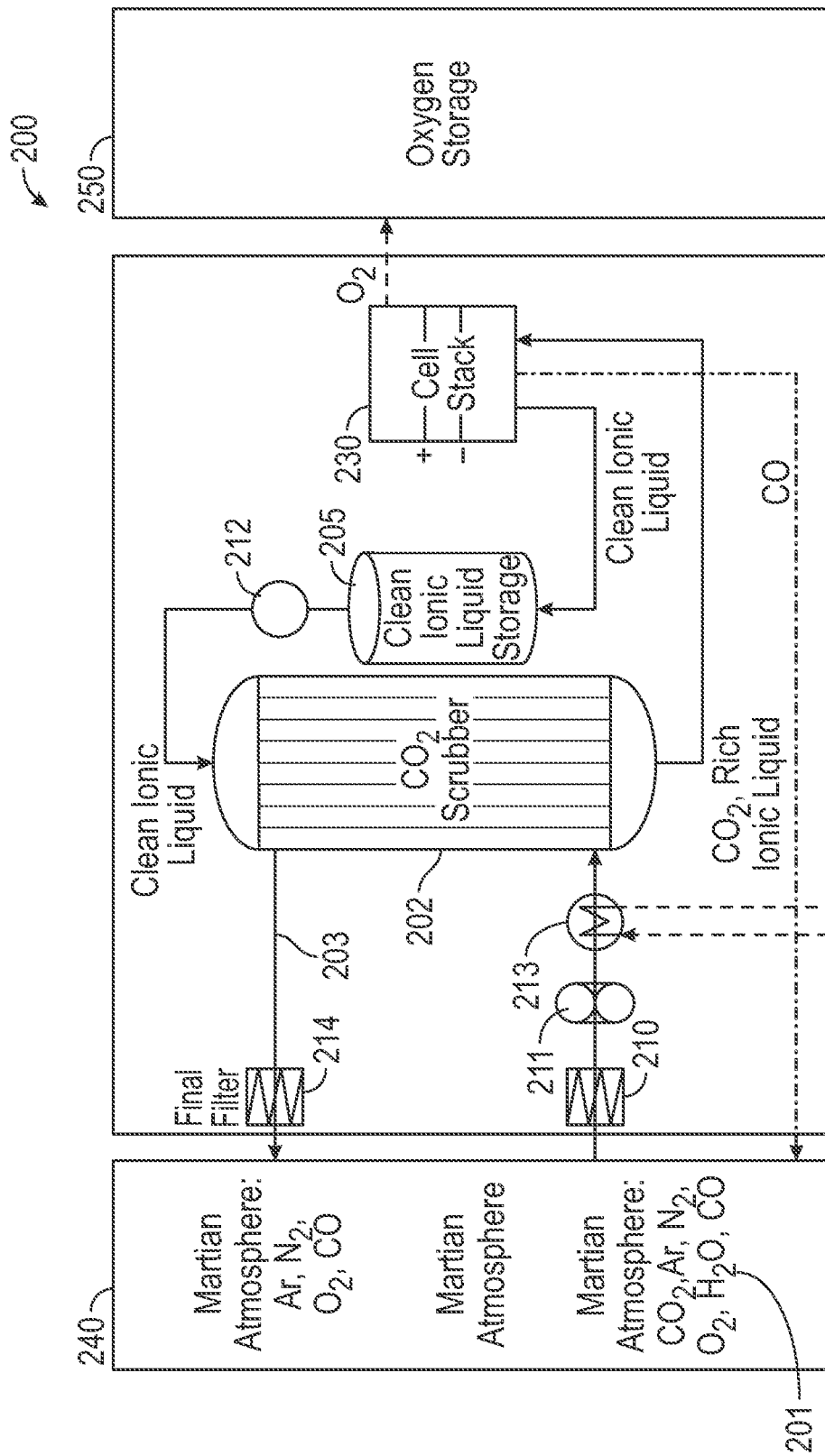
FIG. 2 is a schematic diagram of a carbon dioxide conversion system according to an another embodiment of the present invention.

FIG. 2 is a schematic diagram of another exemplary embodiment of the present invention. FIG. 2 is similar to that described in relation to FIG. 1. Accordingly, reference numbers in FIG. 2 correspond to like reference numbers in FIG. 1.

However, in the exemplary embodiment of FIG. 2, a carbon dioxide conversion system 200 is provided in the context of an environment 240 open to ambient air or gas—such as a Martian atmosphere—as opposed to the closed environment 140 of FIG. 1. In this exemplary instance, the environment 240 is the Martian atmosphere. From the Martian atmosphere 240, feed gas 201 to the system may include CO2, Ar, N2, O2, H2O, CO, and/or other gases present in the Martian atmosphere 240.

In FIG. 2, a scrubber 202 may separate CO2 from the feed gas 201 and discharge a cleaned gas 203 that contains less CO2 than feed gas 201 to the Martian atmosphere 240. The discharged gas 203 may include Ar, N2, O2, CO, and/or other gases present in the Martian atmosphere 240 or produced by the conversion cell(s) 230. An electrochemical conversion cell(s) 230 (or cell stack) may discharge CO into the Martian atmosphere 240, rather than being sent to a CO methanation reactor 115 as in FIG. 1. Also, O2 discharged from the conversion cell(s) 230 can be sent to an oxygen storage unit 250 for eventual use by human occupants in a space craft or habitat, for example. This is in contrast to O2 being sent from the conversion cell 130 to the cabin 140 in FIG. 1.

Figure 3A:
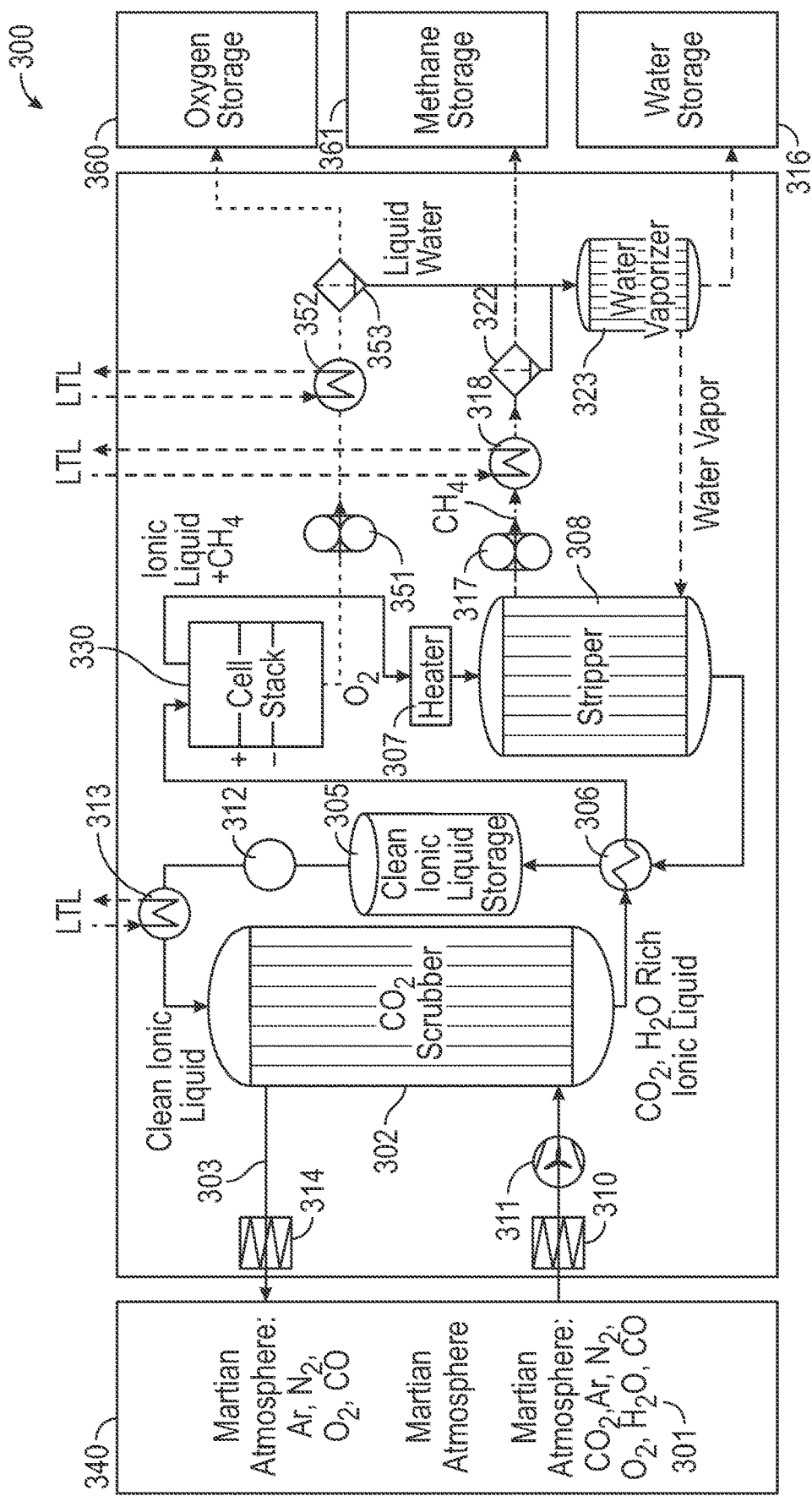
FIGS. 3A-3B are schematic diagrams of a carbon dioxide conversion system according to a further embodiment of the present invention.

FIG. 3A is a schematic diagram of another exemplary embodiment of the present invention. FIG. 3A is similar to that described in relation to FIG. 2. Accordingly, reference numbers in FIG. 3A correspond to like reference numbers in FIG. 2.

However, in the embodiment of FIG. 3A, a cooler 313 may be intermediate a pump 312 and a scrubber 302, whereas there is no similar cooler in FIG. 2. A heat exchanger 306 may be intermediate the scrubber 302, a clean ionic liquid storage 305, an electrochemical conversion cell(s) 330 (or cell stack), and a second gas-liquid contactor-separator (i.e., stripper) 308. In the embodiment of FIG. 2, there is no similar heater or stripper.

Accordingly, in the embodiment of FIG. 3A, the scrubber 302 may discharge a used liquid absorbent having CO2 and H2O, for example. That used liquid absorbent can be received by the heat exchanger 306 and then discharged to the conversion cell(s) 330. Concurrently with, or sequentially with, the foregoing, the heat exchanger 306 may receive cleaned liquid absorbent from the stripper 308 and discharge the same to the clean ionic liquid storage 305. Thus, cleaned liquid absorbent can be pumped into the scrubber 302 where CO2 is separated from the feed gas 301, and discharge cleaned gas 303 containing Ar, N2, O2, CO, and/or other gases present in the Martian atmosphere 340 or produced by the conversion cell(s) 330 may be discharged into the Martian atmosphere.

The electrochemical conversion cell(s) 330, upon receiving the ionic liquid with CO2 and H2O from the scrubber 302 and performing electrochemical conversions, may discharge ionic liquid with CH4 to a heater 307, and the same may then flow to the stripper 308. CH4 may exist in the discharged ionic liquid as a result of the characteristics of the cathode and solubility of CH4 in the ionic liquid. The stripper 308 may remove CH4 from the ionic liquid to thereby discharge cleaned ionic liquid that can flow into the ionic liquid storage 305. The CH4 removed by the stripper 308 may be discharged to a pump 317, a condenser 318, and a water extractor 322 for receipt by a methane storage 361. The system may also be operated without heater 307, stripper 308, and pump 317, where gaseous products of the conversion cell(s) 330 cathode are discharged to condenser 318 if solubility of CH4 in the ionic liquid is low. Stored methane may then be used as fuel in a space craft, for example.

Concurrently with, or sequentially with, the conversion cell(s) 330 discharging ionic liquid with CH4, the conversion cell(s) 330 may also discharge O2 through a pump 351, a condenser 352, and a water extractor 353 for receipt by an oxygen storage 360. Stored oxygen may then be used by human occupants in a space craft, for example.

From the water extractor 353, liquid water may flow to a water vaporizer 323. Discharged liquid water therefrom may be received in a water storage 316, while discharged water vapor therefrom may flow to the stripper 308 wherein the water vapor can be used as a sweep gas.

Figure 3B:
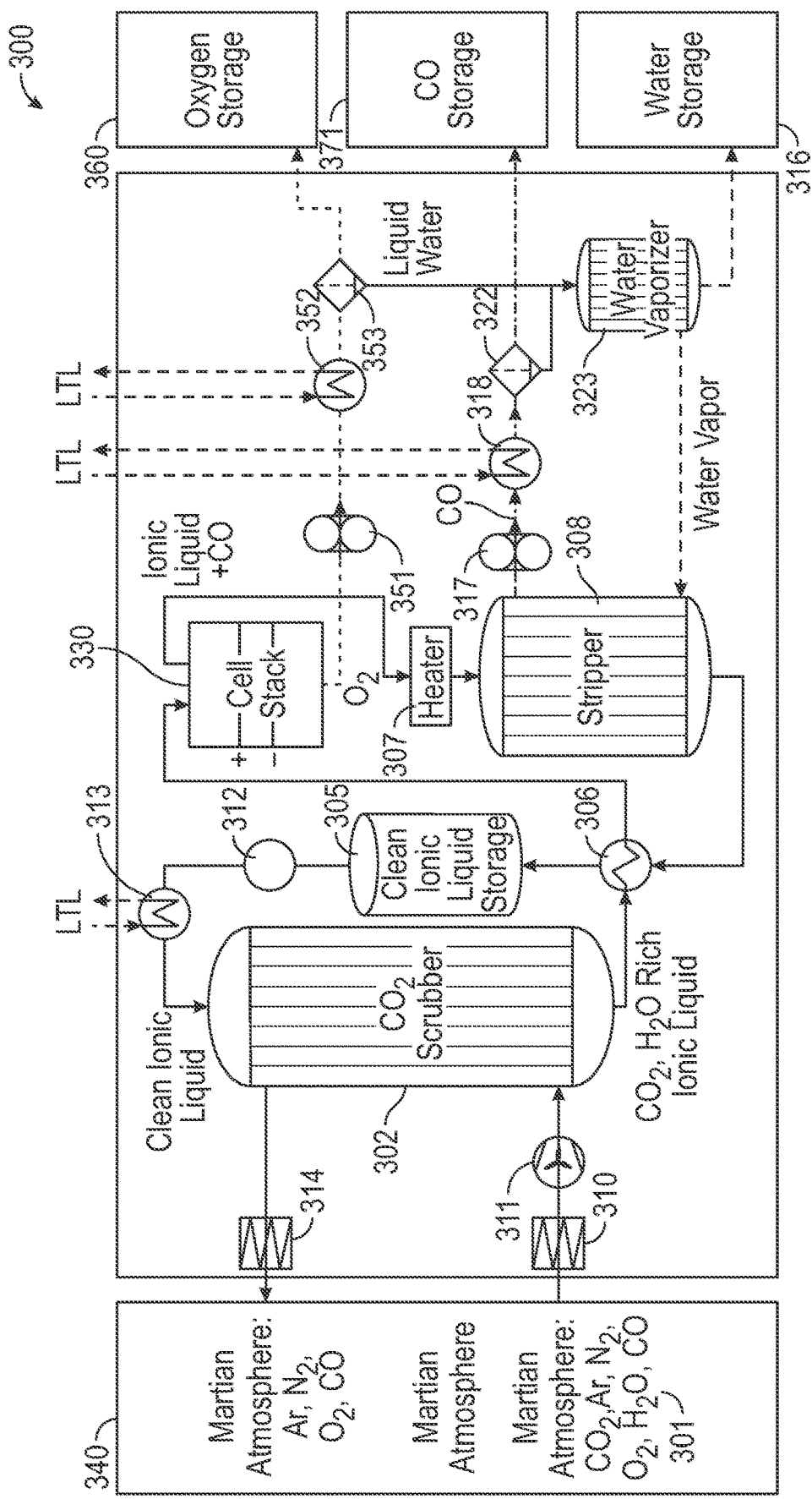

FIG. 3B is a schematic diagram of another exemplary embodiment of the present invention. FIG. 3B is similar to that described in relation to FIG. 3A. Accordingly, reference numbers in FIG. 3B correspond to like reference numbers in FIG. 3A.

The embodiment of FIG. 3B is largely the same as the embodiment of FIG. 3A. However, in FIG. 3B, the electrochemical conversion cell(s) 330 discharges ionic liquid with CO rather than with CH4 as in FIG. 3A. Thus, the stripper 308 discharges CO rather than CH4. And the discharged CO is received by a CO storage 371 for eventual use by human occupants in a space craft or habitat, for example.

The invention could also be used in several other configurations.

In one embodiment, the anode compartment contains ionic liquid and/or an aqueous electrolyte solution. O2 is recovered through a gas diffusion electrode directly as O2 in FIGS. 3A and 3B, or by passing the solution from the anode compartment through a stripper, pump, compressor, and water extractor as in methane and CO FIGS. 3A and 3B.

In this embodiment, the anode compartment does not contain an IL or aqueous solution separate from the solution in the cathode compartment. Instead, water or hydroxide passes through the ion exchange membrane or porous separator from the cathode compartment and is electrolyzed on the anode surface to O2. This removes the need for O2 separation from an electrolyte solution. O2 is recovered as in O2 in FIGS. 3A and 3B.

In CO2 removal applications where closed-loop O2 recovery is unnecessary (e.g., aircraft, submarines), electrochemical H2 and CO fuel production could be targeted. The O2, H2, and CO products could be collected for use in fuel cells.

Figure 4B:
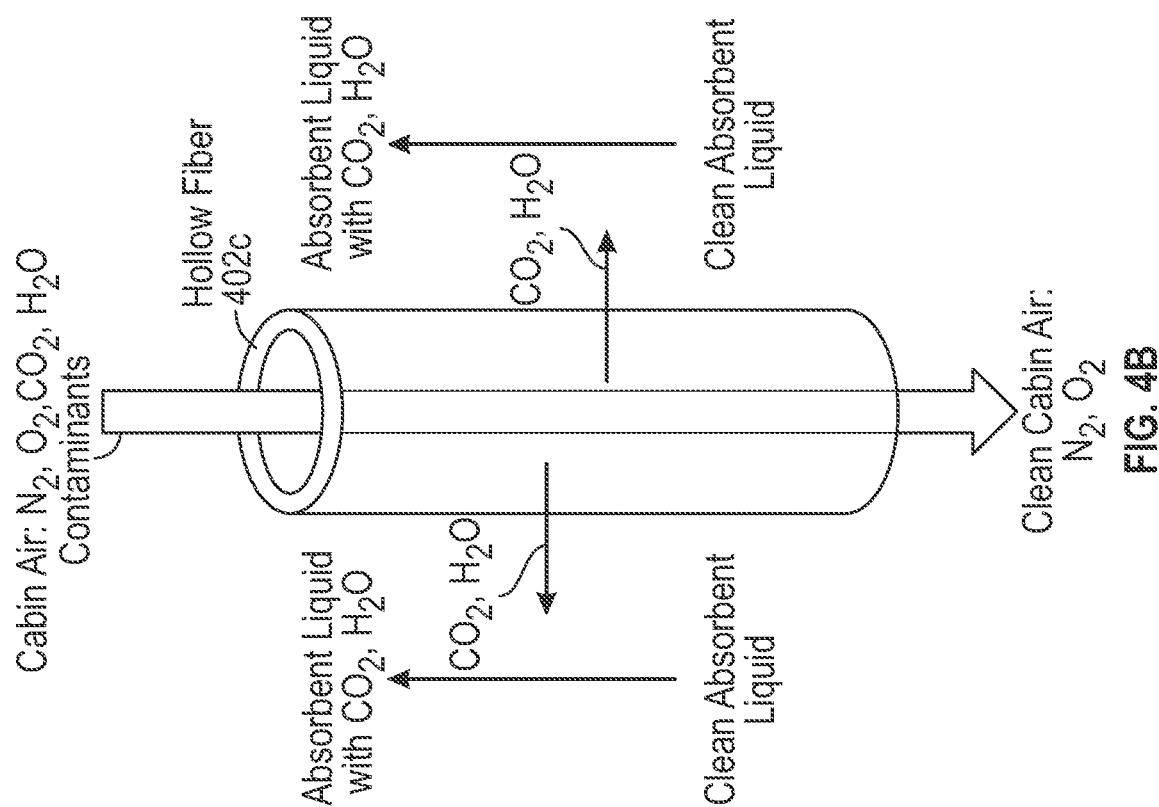
FIGS. 4A-4B are side views of a scrubber according to an embodiment of the present invention.
Figure 4A:
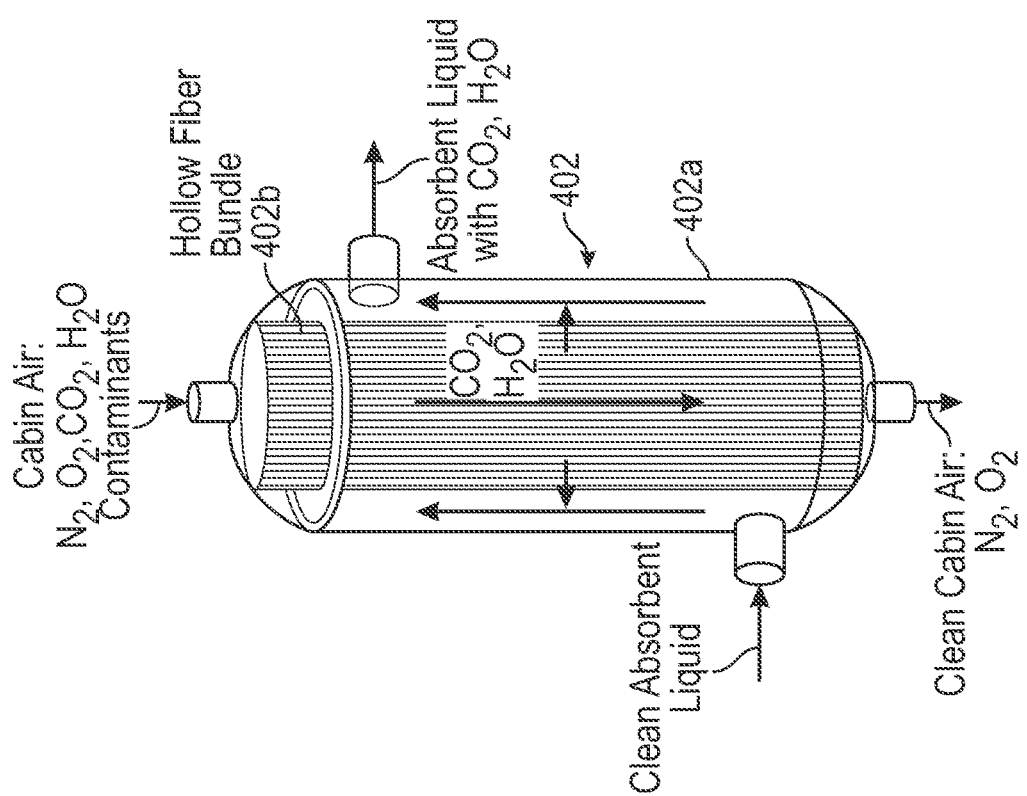

FIGS. 4A-4B depict an exemplary embodiment of a scrubber 402 that may be employed in the carbon dioxide conversion system 100, for example. In FIG. 4A, the scrubber 402 may include a cylindrical housing 402a that encloses a hollow fiber bundle 402b. CO2-rich gas may enter the housing 402a at one end thereof and CO2-lean gas may exit at an opposite end thereof. Regenerated or cleaned liquid absorbent may enter the housing 402a at one side thereof, and used liquid absorbent with carbon dioxide may exit the housing 402a at an opposite side thereof. In this embodiment, regenerated or cleaned absorbent liquid flows counter (i.e., opposite) to the gas flow. Moreover, the counter flow causes carbon dioxide to flow from the gas out of the hollow fiber bundle 402b into the liquid.

FIG. 4B depicts the same flows as in FIG. 4A, but in the context of a single hollow fiber 402c that can be part of the hollow fiber bundle 402b.

Figure 5B:
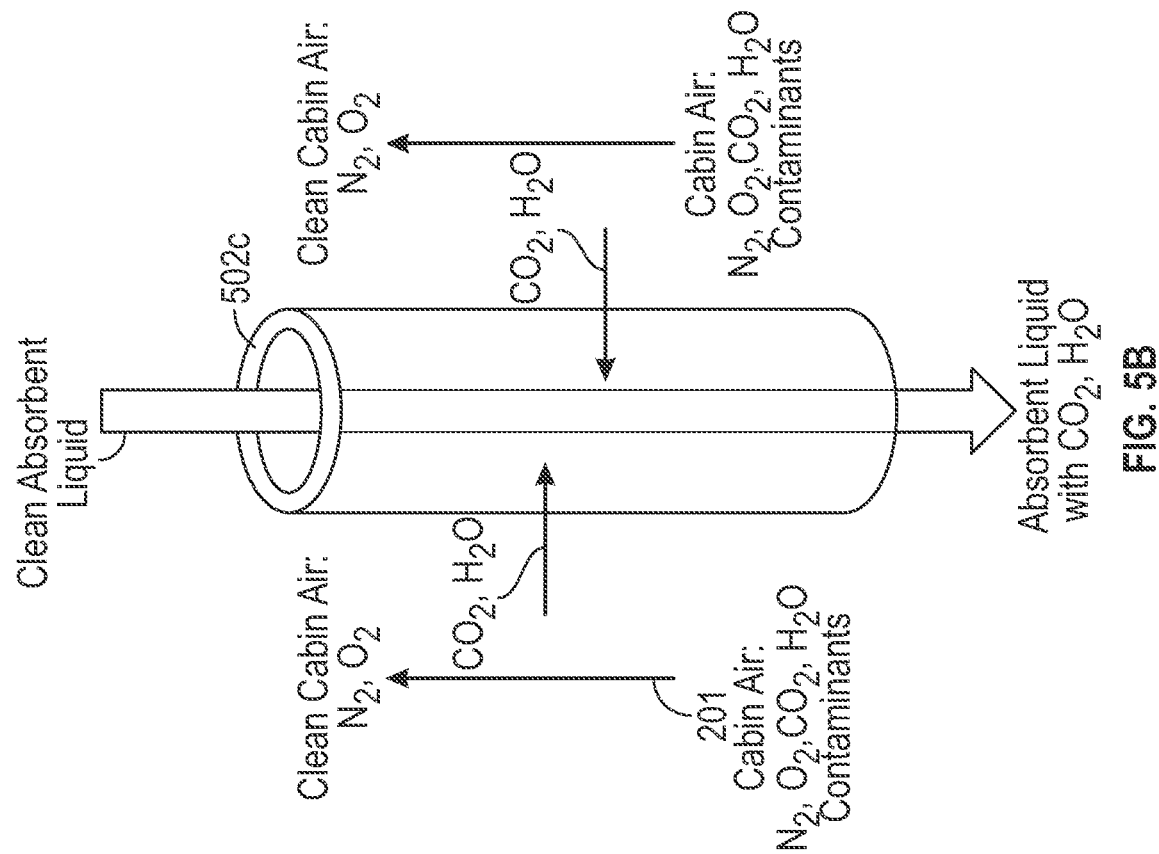
FIGS. 5A-5B are side views of a scrubber according to another embodiment of the present invention.
Figure 5A:
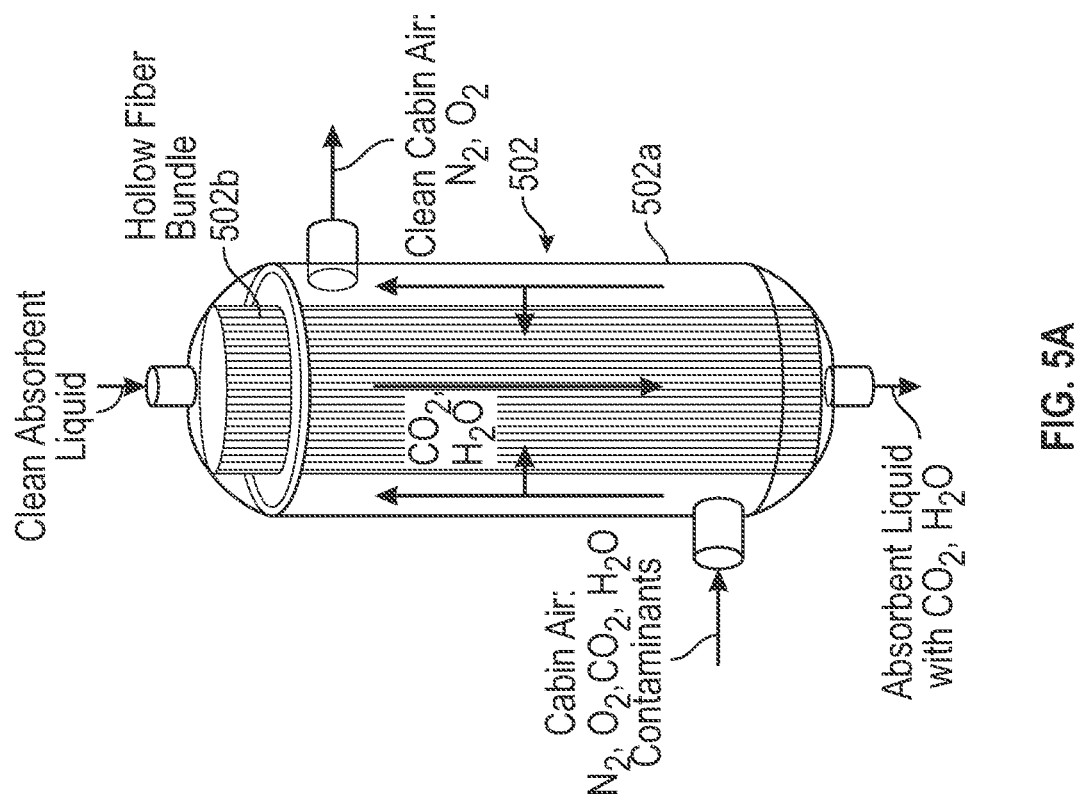

FIGS. 5A-5B depict another exemplary embodiment of a scrubber 502 that may be employed in the carbon dioxide conversion system 100, for example. As in FIG. 4A, in FIG. 5A, the scrubber 502 may include a cylindrical housing 502a that encloses a hollow fiber bundle 502b. However, CO2-rich gas may enter the housing 502a at one side thereof and CO2-lean gas may exit at an opposite side thereof. Regenerated or cleaned absorbent liquid may enter the housing 502a at one end thereof, and used absorbent liquid with carbon dioxide may exit the housing 502a at an opposite end thereof. As in FIG. 4A, in this embodiment, cleaned absorbent liquid flows counter (i.e., opposite) to the gas flow. However, the counter flow causes carbon dioxide to flow from the gas into the liquid in the hollow fiber bundle 502b.

FIG. 5B depicts the same flows as in FIG. 5A, but in the context of a single hollow fiber 502c that can be part of the hollow fiber bundle 502b.

Figure 6B:
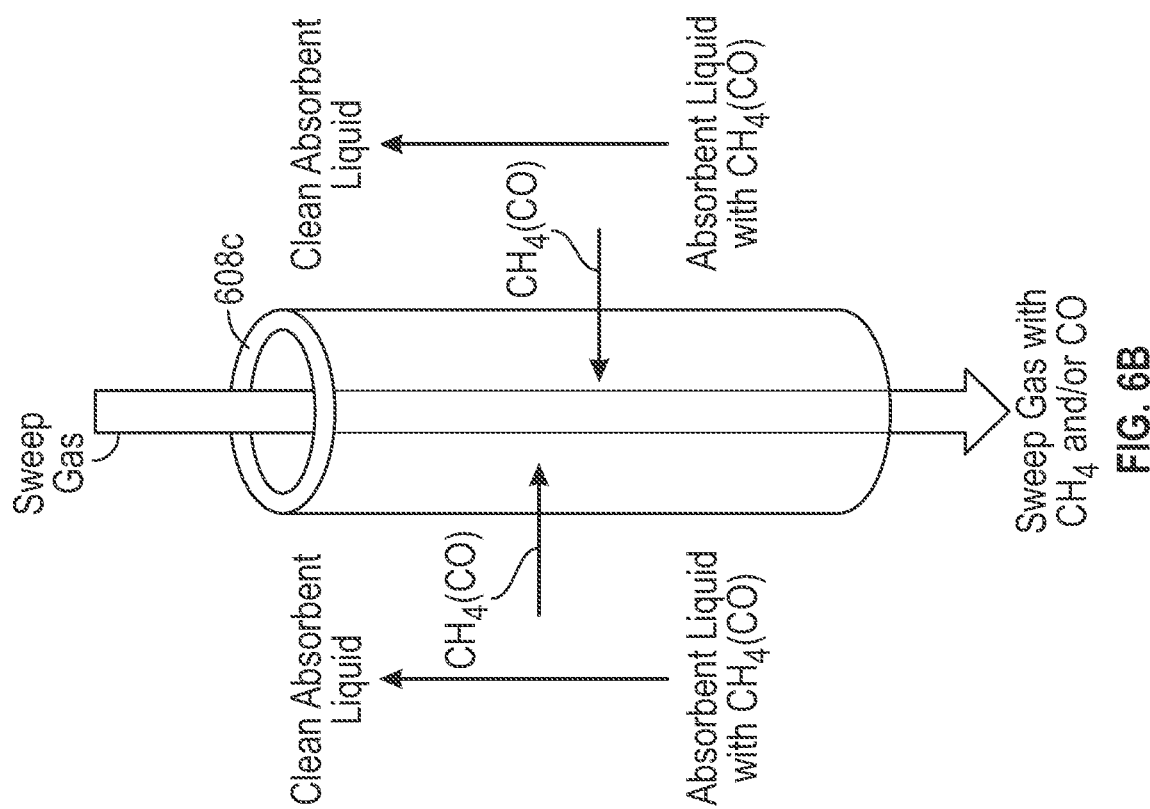
FIGS. 6A-6B are side views of a stripper according to an embodiment of the present invention.
Figure 6A:
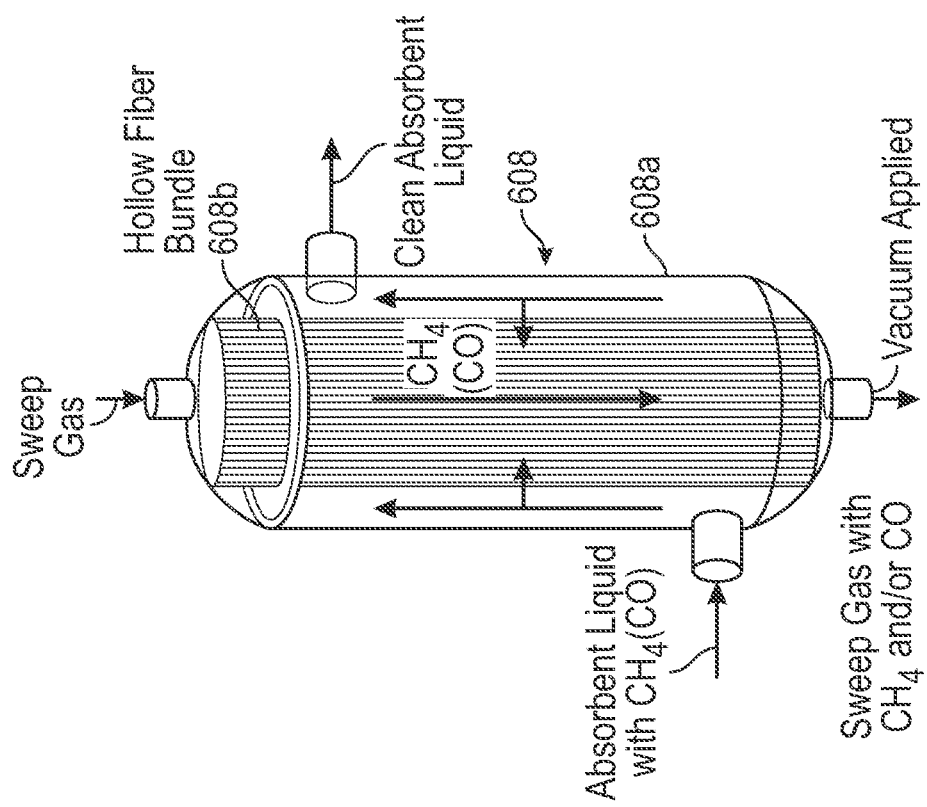

FIGS. 6A-6B depict an exemplary embodiment of a stripper 608 that may be employed in the carbon dioxide conversion system 300, for example. In FIG. 6A, the stripper 608 may include a cylindrical housing 608a that encloses a hollow fiber bundle 608b. Sweep gas may enter the housing 608a at one end thereof and contaminants (CO2, H2O, CH4, and/or CO) may exit at an opposite end thereof. Used absorbent liquid with contaminants may enter the housing 608a at one side thereof, and regenerated or clean absorbent liquid may exit the housing 608a at an opposite side thereof. In this embodiment, used absorbent liquid with contaminants flows counter (i.e., opposite) to the sweep gas flow. Moreover, the counter flow causes contaminants to flow from the liquid into the gas in the hollow fiber bundle 608b.

FIG. 6B depicts the same flows as in FIG. 6A, but in the context of a single hollow fiber 608c that can be part of the hollow fiber bundle 608b.

Figure 7B:
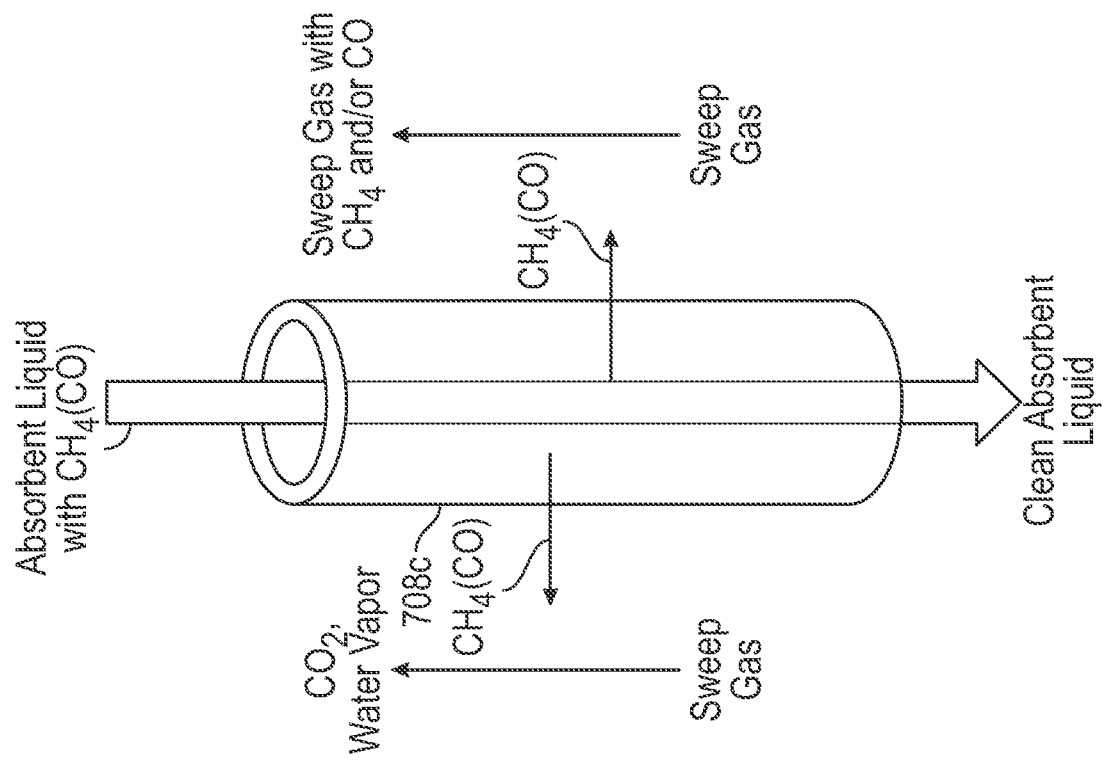
FIGS. 7A-7B are side views of a stripper according to another embodiment of the present invention.
Figure 7A:
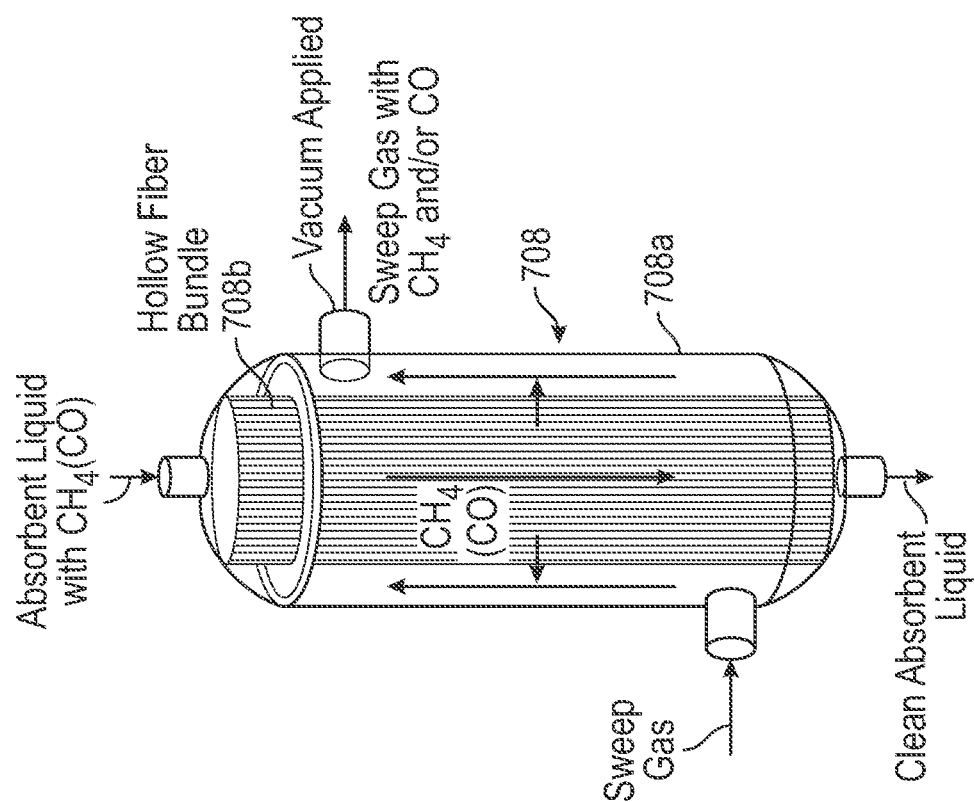

FIGS. 7A-7B depict another exemplary embodiment of a stripper 708 that may be employed in the carbon dioxide conversion system 300, for example. As in FIG. 6A, in FIG. 7A, the stripper 708 may include a cylindrical housing 782a that encloses a hollow fiber bundle 708b. However, sweep gas may enter the housing 708a at one side thereof and contaminants may exit at an opposite side thereof. Used absorbent liquid with contaminants may enter the housing 708a at one end thereof, and regenerated or clean absorbent liquid may exit the housing 708a at an opposite end thereof. As in FIG. 6A, in this embodiment, sweep gas flows counter (i.e., opposite) to the used absorbent liquid with contaminants flow. However, the counter flow causes contaminants to flow from the liquid out from the hollow fiber bundle 708b into the gas.

FIG. 7B depicts the same flows as in FIG. 7A, but in the context of a single hollow fiber 708c that can be part of the hollow fiber bundle 708b.

According to the present invention, the liquid absorbent can meet a demanding set of criteria. The liquid can be safe and nontoxic to humans, and may not contaminate the purified air with odors or organic vapors. It may absorb carbon dioxide at the partial pressure expected during the mission, and may not lose performance when simultaneously absorbing water. It may also be regenerable without the use of space vacuum, so as not to lose CO2 and water to space, and regenerable without using excessive temperatures or power. The liquid may be durable and last without deterioration for the life of the mission. Since the liquid also serves as the electrolyte in the electrochemical cell, it may have appreciable electrical conductivity, and it may be stable with respect to electrochemical oxidation or reduction within the potential window for the process.

The liquid absorbent can be one or more ionic liquids. They are salts, generally comprised of an anion and organic cation, which are liquid at their temperature of use. Because they are salts, they have effectively zero vapor pressure, thus eliminating odors and reducing the likelihood of contaminating the purified air. Also, because they are salts, they have good electrical conductivity. They are generally nontoxic and have sufficient stability to resist deterioration. Ionic liquids generally contain relatively large organic cations (quaternary ammonium or phosphonium compounds) and any of a variety of anions, both of which can be tailored to obtain desired characteristics. Ionic liquids can both physically dissolve carbon dioxide and have specific chemical interactions with it. Interactions of some ionic liquids with carbon dioxide and electrode surfaces favor electrochemical conversion of carbon dioxide into specific products. As a class, almost every ionic liquid is water soluble and hygroscopic, meaning that they will absorb moisture from the air, but due to their negligible volatility, the water can be removed by evaporation either by elevating the temperature or reducing the water partial pressure. Because a very large number of ionic liquids exist, and both the cation and the anion can be tailored to obtain desired characteristics, this class of compounds has flexibility as the liquid absorbent and electrolyte for a carbon dioxide removal and conversion system.

Ionic liquids suitable for use in this invention comprise those with melting points below 20° C., low vapor pressure, and with capacity for carbon dioxide, at 30° C. and in the presence of 3.8 torr carbon dioxide partial pressure, of >0.3 wt %. Examples of such ionic liquids include 1-ethyl-3-methylimidazolium acetate, 1-ethyl-3-methylimidazolium trifluoracetate, 1-butyl-3-methylimidazolium acetate, tributylmethylphosphonium acetate, triethylmethylphosphonium acetate etc. These ionic liquids are hygroscopic and can absorb water as well and carbon dioxide. Therefore, the effective working fluid can, in many cases, comprise a mixture of the ionic liquids specified and water. It may, under some circumstances, be useful to add water to the ionic liquid before contacting with carbon dioxide. This can reduce the carbon dioxide capacity but also reduce the viscosity.

1-butyl-3-methylimidazolium acetate (BMIM Ac) has a high $CO_2$ capacity and well understood physical properties. BMIM Ac satisfies the basic requirements for an absorbent in a manned vehicle. It is not a hazardous substance or mixture, and has no hazards not otherwise classified. The pH of an aqueous solution is 6.1, and the autoignition temperature is 435° C. The compound is a clear, somewhat viscous liquid, and can be handled readily. The surface tension is similar to that for a polar organic solvent, and the density is similar to that for water. The onset for thermal degradation sets the upper temperature limit for processing, and is comfortably higher than the temperature needed for desorption. The viscosity for this ionic liquid is higher than that of water, but can be reduced by raising either the temperature or water content. In normal use, the ionic liquid absorbs both $CO_2$ and water, and therefore the viscosity values vary in the presence of water. Viscosity plays a role in determining mass transfer rates for $CO_2$ adsorption and desorption. Control of viscosity can therefore reduce the weight and volume of the contactor-separator.

According to the present invention, a significant increase in $O_2$ recovery could be a game-changer for NASA and commercial interests pursuing travel to Mars or space habitation. Electrochemical technology may significantly decrease the amount of $O_2$ (and/or water) that will be required to be brought on each mission. This saves both space on the vessel and launch weight. In addition, the present invention may require less power than alternative $CO_2$ conversion technologies for recovery of the same amount of $O_2$.

It should be understood, of course, that the foregoing relates to exemplary embodiments of the invention and that modifications may be made without departing from the spirit and scope of the invention as set forth in the following claims.

We claim:

1. A carbon dioxide conversion system for an environment that is ambient gas, comprising:
    a scrubber downstream of the environment;
    an electrochemical conversion cell downstream of the scrubber;
    an ionic liquid storage intermediate the scrubber and the electrochemical conversion cell;
    a stripper intermediate the electrochemical conversion cell and the ionic liquid storage, wherein:
        the scrubber is configured to receive gas containing carbon dioxide from the environment, receive cleaned liquid absorbent from the ionic liquid storage, and discharge at least one of Ar, N2, and CO to the environment, and
        the stripper is configured to (i) use water vapor as a sweep gas, (ii) discharge cleaned liquid absorbent to the ionic liquid storage, and (iii) discharge methane to a methane storage.

2. The system of claim 1, further comprising a water vaporizer upstream of the stripper.

3. The system of claim 1, wherein the electrochemical conversion cell is configured to discharge $O_2$ to an oxygen storage.

4. The system of claim 3, further comprising:
    a water extractor disposed intermediate the electrochemical conversion cell and the oxygen storage, the water extractor configured to extract water from the oxygen.

5. The system of claim 4, further comprising:
    a water vaporizer downstream of the water extractor and configured to discharge (i) liquid water to a water storage and (ii) water vapor to the stripper.

6. The system of claim 1, wherein the scrubber is further configured to discharge used liquid absorbent having $CO_2$ and $H_2O$.

7. The system of claim 1, further comprising a heater disposed intermediate the electrochemical conversion cell and the stripper.

\* \* \* \* \*